(12) United States Patent
Botnar et al.

(10) Patent No.: US 11,079,456 B2
(45) Date of Patent: Aug. 3, 2021

(54) METHOD OF RECONSTRUCTING MAGNETIC RESONANCE IMAGE DATA

(71) Applicants: Siemens Healthcare GmbH, Erlangen (DE); King's College London, London (GB)

(72) Inventors: Rene Botnar, London (GB); Aurelien Bustin, London (GB); Radhouene Neji, London (GB); Claudia Prieto, London (GB)

(73) Assignee: Siemens Healthcare GmbH, Erlangen (DE)

( * ) Notice: Subject to any disclaimer, the term of this patent is extended or adjusted under 35 U.S.C. 154(b) by 55 days.

(21) Appl. No.: 16/409,070

(22) Filed: May 10, 2019

(65) Prior Publication Data
US 2019/0346522 A1    Nov. 14, 2019

(30) Foreign Application Priority Data

May 10, 2018 (GB) ...................... 1807623

(51) Int. Cl.
| | | |
|---|---|---|
| *G01R 33/565* | (2006.01) | |
| *G01R 33/48* | (2006.01) | |
| *G06F 17/11* | (2006.01) | |
| *G06T 11/00* | (2006.01) | |

(52) U.S. Cl.
CPC ....... *G01R 33/565* (2013.01); *G01R 33/4822* (2013.01); *G06F 17/11* (2013.01); *G06T 11/006* (2013.01); *G06T 11/008* (2013.01)

(58) Field of Classification Search
CPC .............. G01R 33/565; G01R 33/4822; G01R 33/5676; G01R 33/5611; G01R 33/56509; G01R 33/4826; G06F 17/11; G06T 11/006; G06T 11/008; A61B 5/721; A61B 5/7292; A61B 5/055; G06K 9/6249
See application file for complete search history.

(56) References Cited

U.S. PATENT DOCUMENTS

2017/0112449 A1    4/2017   Huang et al.

FOREIGN PATENT DOCUMENTS

| WO | WO 2015086415 A1 | 6/2015 | |
|---|---|---|---|
| WO | WO 2016014354 A1 | 1/2016 | |
| WO | WO-2016090686 A1 * | 6/2016 | ............. A61B 5/055 |

OTHER PUBLICATIONS

Technical Note: Accelerated nonrigid motion-compensated isotropic 3D coronary MR angiography; Nov. 2017.

(Continued)

*Primary Examiner* — Susan S Lee
(74) *Attorney, Agent, or Firm* — Schiff Hardin LLP

(57) ABSTRACT

A method of reconstructing magnetic resonance (MR) image data from k-space data. The method includes obtaining k-space data of an image region of a subject; and reconstructing, using a sparse image coding procedure, the MR image data from the k-space data by performing an iterative optimization method. The optimization method includes a data consistency iteration step and a denoising iteration step applied to MR image data generated by the data consistency iteration step. The denoising iteration step incorporates a sparsifying operation to provide a sparse representation of the MR image data for the imaged region as an input to the data consistency iteration step.

10 Claims, 4 Drawing Sheets

(56) References Cited

OTHER PUBLICATIONS

Ramani, Satish et al.: "Parallel MR Image Reconstruction Using Augmented Lagrangian Methods"; IEEE Transactions on Medical Imaging; vol. 30; No. 3; Mar. 2011; pp. 694-706.
Henningsson, M. (2013). Prospective respiratory motion correction for coronary MRangiography using a 20 image navigator. Magnetic Resonance in Medicine, 69, pp. 486-494.; 2013.
C. Stehning et al: "Free-Breathing Whole-Heart Coronary MRA With 3D Radial SSFP and Self-Navigated Image Reconstruction", Magnetic Resonance in Medicine 54, pp. 476-480, 2005; 2005.

* cited by examiner

METHOD OF RECONSTRUCTING MAGNETIC RESONANCE IMAGE DATA

TECHNICAL FIELD

The present disclosure relates to a method of reconstructing magnetic resonance (MR) image data, a computer readable medium, and a MR imaging apparatus.

In particular the disclosure is concerned with a method of reconstructing magnetic resonance image data from k-space data, and in particular undersampled k-space data.

BACKGROUND

In magnetic resonance (MR) imaging, imaging data is commonly acquired as samples of the Fourier transform of the subject to be reconstructed. These samples are referred to as "k-space" data. Images are generated from the k-space data using an image reconstruction process which can involve recovering an estimate of the original subject from the k-space data.

Only a limited amount of k-space data may be acquired at any given time. There may also be delays between the k-space data acquisitions due to the time required for the signal excitation and encoding processes inherent to MR imaging. This typically means that the k-space data for an imaging region of the subject is acquired over several respiratory cycles of the subject. This may mean that respiratory motion artefacts are introduced into the k-space data, and as a result the quality of the reconstructed images may be reduced.

Respiratory motion is a particular problem in the free-breathing imaging of a volume region of a subject. One particular application of such is three-dimensional whole-heart coronary MR angiography (CMRA).

Techniques may be used to obtain k-space data for a 2D image region or a 3D image volume. In order to generate k-space data for a 3D image volume, techniques may use a 3D sampling scheme, in which sampling is performed in the $k_x$–$k_y$ plane repeatedly at a succession of positions in the $k_z$ dimension.

The centre of k-space ($k_x$=$k_y$=0 for 2D and $k_x$=$k_y$=$k_z$=0 for 3D) can be used to obtain the temporal variation caused by subject motion. The centre of k-space corresponds to a constant term in the Fourier representation of the image, whose magnitude is the same as the average image brightness. Thus, by comparing the centre of k-space values for the different data acquisitions, the change in the centre of k-space value across the different data acquisitions can be determined, and used to estimate the subject respiratory motion.

As a result, the acquired data may be sorted into multiple respiratory phases. The sorted data of k-space data can then be reconstructed to generate respiratory resolved images.

In particular, each undersampled sorted data set may be used to reconstruct MRI image data using a compressed sensing procedure. For example, a compressed sensing procedure solves an optimization problem of the form:

$$\hat{x} = \underset{x}{\operatorname{argmin}}\left\{\frac{1}{2}\|Ex - k\|_2^2 + \gamma \Psi_t(x)\right\} \quad (1)$$

Here, x is the respiratory-resolved image series, k is the k-space data. The encoding operator E=AFS incorporates the sampling matrix A for the k-space data, Fourier transform F and coil sensitivities S.

Here, $\|.\|_2^2$ denotes the $l_2$-norm defined as $\|u\|_2^2 = \sqrt{(\Sigma_i |u_i|^2)}$, for a given vector u defined by vector components $u_i$.

Here, $\Psi_t$ is a 1D temporal total variation (TV) function applied in the respiratory-resolved direction or a wavelet-based regularization. Here, a is a regularization parameter.

The component $\frac{1}{2}\|Ex-k\|_2^2$ of the optimization problem is known as a data consistency component of the compressed sensing procedure.

The component $\Psi_t(x)$ of the optimization problem is known as a transform sparsity component of the compressed sensing procedure.

The parameter γ is a regularization parameter that determines the trade-off between the data consistency and the sparsity. Such methods have been shown to suffer from reduced image quality when using a Cartesian sampling scheme. The reduced image quality is particularly pronounced for respiratory phases with large respiratory displacements.

It is an objective of the present disclosure to provide an improved approach for reconstructing MR image data from accelerated (i.e. undersampled) k-space data, or at least provide an alternative to the existing reconstruction approaches. It is a particular objective to provide an improved reconstruction approach that is robust to motion even when a Cartesian sampling scheme is used to acquire the undersampled k-space data.

SUMMARY

According to the present disclosure there is provided a method and apparatus as set forth in the appended claims. Other features of the disclosure will be apparent from the dependent claims, and the description which follows.

According to a first aspect of the disclosure, there is provided a method of reconstructing MR image data from undersampled k-space data. The method comprises obtaining k-space data of an image region of a subject, and using a sparse image coding procedure to reconstruct the MR image data from the k-space data by iteratively solving an optimization problem. The iterative solution comprises a data consistency iteration step and a denoising iteration step applied to MR image data generated by the data consistency iteration step. The denoising iteration step incorporates a sparsifying operation to provide a sparse representation of the MR image data for said imaged region as an input to the data consistency iteration step of the optimization problem.

The method may include acquiring a navigator signal, or a plurality of navigator signals for the image region of the subject, and uses the navigator signal(s) to reconstruct the MR image data using the sparse image coding procedure. In this way, a rapid image reconstruction is possible and may provide robustness against subject motion in the reconstruction even if a Cartesian sampling scheme is used. As such, k-space data may be acquired with close to (or even at) 100% scan efficiency.

Generally, the present disclosure uses a denoising iteration to increase sparsity and to reduce image noise. In this way, the present disclosure is able to minimise respiratory motion artefacts and artefacts due to cardiac motion. As such, respiratory and/or cardiac resolved MR image data may be reconstructed.

The k-space data may be acquired over a plurality of cardiac cycles for the subject. Each of the plurality of navigator signals may be acquired during a respective one of the plurality of cardiac cycles.

The acquired k-space data may be sub-sampled (under-sampled) k-space data. By sub-sampled, we mean that the k-space data is acquired using fewer echoes than a conventional MR scan. In other words, only data for part of the k-space is collected. The k-space data may be acquired using an incoherent sampling scheme. This may be so as to create a noise-like appearance for the aliasing artefacts that are generated as a result of the sub-sampling. The noise-like artefacts may be removed in a subsequent step of the optimization procedure.

As explained above, the MR image data is reconstructed from the k-space data using a sparse coding procedure. The sparse coding procedure comprises solving an optimization problem that comprises a data consistency component and a denoising sparsity component, and iteratively solves these two steps.

The data consistency component acts to ensure that the reconstructed MR image data is consistent with the original acquired k-space data. That is, the data consistency component may be a constraint on the optimization problem that takes into account the difference between the MR image data transformed into k-space and the original acquired k-space data. The optimization problem may seek to minimise the difference between the MR image data transformed into k-space and the original acquired k-space data. This minimisation may be subject to other constraints, e.g. the denoising sparsity component.

The denoising sparsity component of the sparse coding procedure acts to increase the sparsity of the MR image data in a sparse representation space represented by a synthesis dictionary. The increase in sparsity corresponds to a diminishing of the aliasing artefacts in the image space. The optimization problem may seek to maximise the sparsity. This maximisation may be subject to other constraints, e.g. the data consistency component.

Thus, the sparse coding procedure refers to a procedure in which MR image data is reconstructed that is both consistent with the original acquired k-space data and also forms a sparse representation in a synthesis dictionary.

The data consistency iteration step preferably comprises minimising an Augmented Lagrangian with respect to the reconstructed MR image data.

The denoising iteration step preferably comprises minimising an Augmented Lagrangian with respect to sparse coefficients associated with a synthesis dictionary for the sparse representation of the MR image data. Significantly, this implements a synthesis dictionary learning method, in which the dictionary and a corresponding sparse representation are jointly learned from the data.

In synthesis dictionary learning the goal is to simultaneously find a dictionary and corresponding sparse coefficients to represent the data.

A dictionary is a collection of atoms $D=[d_1^T, \ldots, d_n^T]^T$ where $d_i$ is the $i^{th}$ dictionary atom. The image data ($x_i$) is to be represented as a linear combination over the dictionary:

$$x_i \approx D\alpha^i = \sum_{k=1}^{n} d_k \alpha_k^i$$

Here, $\alpha^i=[\alpha_1^i, \ldots, \alpha_n^i]^T$ is the coefficient vector associated with the signal. Synthesis dictionary learning is typically formulated as an optimization problem, where the goal is to find D and sparse coefficients $\{\alpha^i\}$ that minimize the image reconstruction error. Sparse coding provides a class of algorithms for finding succinct representations in image reconstruction. The goal of sparse coding is to represent input vectors approximately as a weighted linear combination of a small number of (unknown) "basis vectors." These basis vectors thus capture high-level patterns in the input data. Sparse coding is a method for discovering good basis vectors automatically. Sparse coding algorithms identify/learn basis functions that capture higher-level features in the data. FIG. 3 schematically represents the relationship between an input vector of image data ($x_i$) and the coefficient vector ($\alpha^i$) via the dictionary matrix (D). Note how the coefficient vector is much more sparse (i.e. contains more zero-valued elements) than is the input vector of image data. It is the appropriate choice of dictionary matrix that permits this.

The data consistency iteration step may comprise a determination of the difference between the reconstructed MR image data transformed into k-space and the acquired k-space data. The determination of the difference may comprise determining the $l_2$-norm of the result of the subtraction of the acquired k-space data from the reconstructed MR image data transformed into k-space.

The denoising iteration step may comprise a determination of the difference between the reconstructed MR image data and the sparse representation of the MR image data. The determination of the difference may comprise determining the $l_2$-norm of the result of the subtraction of the sparse representation of the MR image data from the reconstructed MR image data.

The data consistency iteration step of the optimization problem may be of the form:

$$\hat{x} = \underset{x}{\mathrm{argmin}}\, f(x),$$

where $f(x)$ is a function defined as:
{data consistency component in k-space+$\mu$(sparse consistency component in image space)}

Here, $\mu$ is a regularization parameter.

The denoising iteration step of the optimization problem may be of the form:

$$\hat{x} = \underset{x}{\mathrm{argmin}}\, h(x),$$

where h(x) is a function defined as:
{sparse consistency component in image space+$\lambda$(sparse coefficients associated with a synthesis dictionary for the sparse representation of the MR image data)}, Here, $\lambda$ is a sparsity-control parameter the value of which is adjustable to adjust the strength of sparsity for the sparse representation of the MR image data.

The sparsifying operation of the denoising iteration step may be applied to sparse coefficients associated with a synthesis dictionary for the sparse representation of the MR image data. For example, sparse coefficients having a value below a threshold value may be set to zero. The threshold value may be equal to the value of the sparsity-control parameter of the function h(x) defined above.

The data consistency iteration step of the optimization problem may comprise a determination of the difference between the reconstructed MR image data, x, and the k-space data, k.

The data consistency iteration step may comprise a determination of the difference between the reconstructed MR image data, x, transformed into k-space and the k-space data, k.

The determination of the difference may comprise determining the $l_2$-norm of the result of a subtraction of the k-space data from the reconstructed MR image data transformed into k-space.

The data consistency iteration step may comprise the function $\frac{1}{2}\|Ex-k\|_2^2$, wherein x is the reconstructed MR image data,
wherein k is the k-space data,
wherein E is an encoding operator for transforming the reconstructed MR image data into k-space, and
wherein $\|.\|_2^2$ denotes the $l_2$-norm defined as $\|u\|_2^2 = \sqrt{(\Sigma_i |u_i|^2)}$, for a given vector u.

The encoding operator may be defined as E=AFS. The encoding operator may thus incorporate the sampling matrix A, Fourier transform F and coil sensitivities S.

The generation of reconstructed MR image data is iteratively subject to the denoising/sparsifying effects of the denoising iteration step. In other words, the denoising/sparsifying iteration step imposes on reconstructed MR image data a denoising and sparsifying effect during iterations to converge on a reconstructed MR image data result. Significantly, this helps increase signal-to-noise ratio and reduce artefacts while maintaining accuracy.

The optimization problem may be of the form of an Augmented Lagrangian:

$$\mathcal{L}(x, \alpha) = \underset{x,\alpha}{\operatorname{argmin}}\left\{\frac{1}{2}\|Ex-k\|_2^2 + \lambda\|\alpha\|_0 + \frac{\mu}{2}\|x-D\alpha-b\|_2^2\right\} \quad (2)$$

Here, $\lambda$ is a sparsity-control parameter the value of which is adjustable to adjust the strength of sparsity for the sparse representation of the MR image data, $\mu$ is a regularization parameter, $\alpha$ is a (sparse) coefficient vector associated with a dictionary matrix (D), and b is the Augmented Lagrangian multiplier. In equation (2) the optimization problem incorporates the sparsifying information in the data consistency component via sparse coefficients (a).

The data consistency iteration step may be of the form of an Augmented Lagrangian:

$$\mathcal{L}_1(x) = \underset{x}{\operatorname{argmin}}\left\{\frac{1}{2}\|Ex-k\|_2^2 + \frac{\mu}{2}\|x-D\alpha-b\|_2^2\right\} \quad (3)$$

In equation (3) the iteration incorporates the sparsity via vector $\alpha$, the (sparse) coefficient vector.

The denoising iteration step may be of the form of an Augmented Lagrangian:

$$\mathcal{L}_2(\alpha) = \underset{\alpha}{\operatorname{argmin}}\left\{\frac{1}{2}\|x-D\alpha-b\|_2^2 + +\lambda\|\alpha\|_0\right\} \quad (4)$$

In equation (4) the iteration enforces sparsity on the vector $\alpha$, the (sparse) coefficient vector, via $\lambda$ which is the sparsity-control parameter the value of which is adjustable to adjust the strength of sparsity for the sparse representation of the MR image data.

The sparse image coding procedure may comprise using the output (vector $\alpha$) from the denoising iteration step (equation (4)) as an input to the data consistency iteration step (equation (3)).

The sparse image coding procedure may comprise using the output (b, the Augmented Lagrangian multiplier) from the denoising iteration step (equation (4)) as the Augmented Lagrangian multiplier in the data consistency iteration step (equation (3)).

The sparse image coding procedure may comprise using the de-noised output (the de-noised MR image data) from the denoising iteration step (equation (4)) as the reconstructed MR image data (x) in the data consistency iteration step (equation (3)).

The sparse image coding procedure may comprise using the output (x, the reconstructed MR image data) from the data consistency iteration step (equation (3)) as the reconstructed MR image data in the denoising iteration step (equation (4)).

The k-space data may be acquired using a Cartesian sampling scheme, which may be a spiral sampling scheme. The k-space data may be acquired using a golden-step Cartesian trajectory with spiral profile ordering. Significantly, spiral sampling schemes densely sample the central region of k-space and the centre of k-space itself, is sampled multiple times. Cartesian sampling offers benefits over other sampling (e.g. radial) in many applications. These benefits include a higher signal-to-noise ratio efficiency, i.e. per unit of measurement time, lower sensitivity to off-resonance and gradient delays, and reduced reconstruction complexity.

The navigator signals may be generated from image navigator pulses. The image navigator pulses may be 1 D, 2D, or 3D image navigator pulses.

The k-space data may be for a 2D image region of the subject, or may be for a 3D image region of the subject.

The navigator signals may be 1 D, 2D, or 3D navigator signals.

In a second aspect, the disclosure provides a computer readable medium having instructions recorded thereon which, when executed by a computing device, cause the computing device to perform the method described above.

In a third aspect, the disclosure provides a magnetic resonance, MR, apparatus comprising a computing system, a gradient system, and an excitation system. The gradient system is configured to apply a magnetic field gradient, wherein the excitation system is configured to apply an excitation pulse to the subject and to receive signals from the subject. The computing system is in communication with the excitation system, and the gradient system for controlling these components, and is configured to receive the signals from the excitation system, The computing system is further configured to execute program code to control the gradient system and the excitation system to acquire k-space data of an image region of a subject. The computing system is further configured to use a sparse image coding procedure to reconstruct the MR image data from the acquired k-space data by iteratively solving an optimization problem comprising a data consistency iteration step and a denoising iteration step applied to MR image data generated by the data consistency iteration step. The denoising iteration step incorporates a sparsifying operation to provide a sparse representation of the MR image data for said imaged region as an input to the data consistency iteration step of the optimization problem. The computing system may be further configured to obtain a plurality of navigator signals for the image region of the subject.

BRIEF DESCRIPTION OF THE DRAWINGS

Examples of the present disclosure will now be described with reference to the accompanying drawings, in which.

DETAILED DESCRIPTION

The present disclosure relates to compressed sensing procedures which comprise solving optimization problems comprising a data consistency component and a transform sparsity component.

By way of example, a compressed sensing procedure suitable for use with the present disclosure will now be described which comprises the following steps (1) to (3).

In step (1) of this example sparse image coding procedure, the original acquired k-space data is transformed into MR image data (e.g. a MR image), e.g. through use of a standard iterative SENSE reconstruction, which consist of solving equation (3) without priors (b=Dα=0). SENSE (SENSitivity Encoding) is a well-known imaging technique, readily available to the skilled person, which incorporates knowledge of the sensitivities of the coil elements. The MR image data may suffer from sub-sampling artefacts. However, if an incoherent sampling scheme is used to acquire the k-space, these artefacts may appear to be 'smeared' over the image. That is, almost homogeneous noise-like artefacts may appear in the MR image data. The reconstructed MR image data may serve as a starting point for the optimization problem. The optimization problem seeks to find a better solution (a better set of MR image data) that is also consistent with the original acquired k-space data.

In step (2) a data consistency iteration step is performed according to an Augmented Lagrangian using as input the image data obtained from a denoising iteration step (4), below as image data input.

In step (3) a denoising iteration step is performed according to an Augmented Lagrangian using as input the image data obtained from step (2), above. A sparse representation of the image data is applied in step (3) by removing low-value coefficients of the coefficient vector associated with a synthesis dictionary representation of the image data. The purpose of the sparse representation is to attempt to locally separate the desired signal from the noise artefacts. A higher sparsity means that the useful image content is concentrated in a few pixels, while most of the pixels have only a very low signal.

In step (3), the coefficient vector is thresholded to remove noise.

Figure 3:
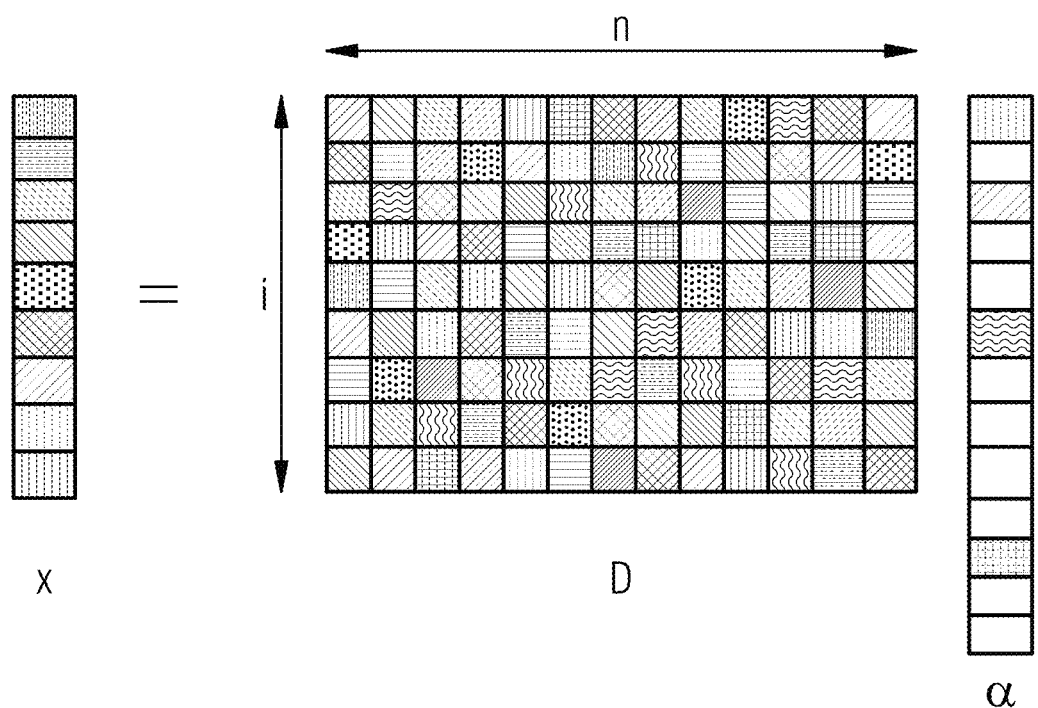
FIG. 3 shows a schematic representation of a synthesis dictionary in a sparse representation of image data.

One example thresholding procedure which may be used is referred to as 'hard thresholding' in which all coefficients of the coefficient vector with a value less than the threshold are set to zero. As a result of the thresholding procedure, many coefficients of the coefficient vector have a value of 0, and as such there are fewer non-zero coefficients of the coefficient vector. Consequently, the sparsity of the image represented in terms of the coefficients of the coefficient vector is increased. This is schematically illustrated in FIG. 3 in which most of the coefficients of the coefficient vector ($\alpha$) are zero-valued, even though this represents the image data vector (x) which has no zero valued coefficients/elements. In FIG. 3, zero-values are represented by non-shaded (empty) elements in the schematic vectors (x, and $\alpha$) and schematic synthesis dictionary (matrix D), and non-zero values are represented by shaded (occupied) elements.

The following examples may use the sparse image coding procedure of the form as described generally above. It will further be appreciated that the present disclosure is not directed towards a particular sparse image coding procedure, but rather the beneficial incorporation sparsity in images of the subject obtained from the plurality of navigator signals into the data consistency and denoising/sparsity iteration steps of the optimization problem of the sparse image coding procedure.

Figure 1:
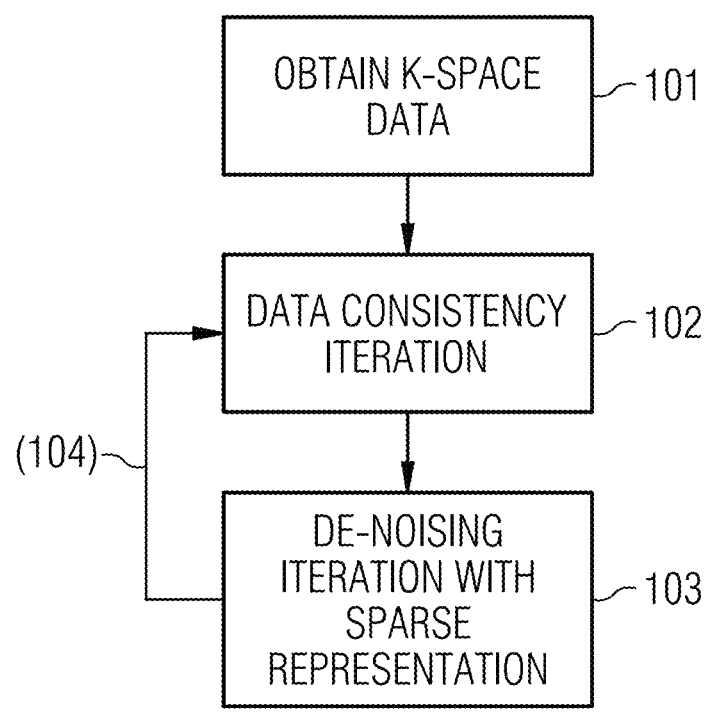
FIG. 1 shows a process diagram for an example method according to the first aspect of the present disclosure.

Referring to FIG. 1, there is shown a method of reconstructing MR image data from k-space data.

Step 101 comprises obtaining k-space data of an image region of a subject.

In the example of FIG. 1, the k-space data is three-dimensional (3D) whole-heart coronary MR angiography data (CMRA) acquired using a Cartesian trajectory. The Cartesian trajectory samples the $k_y$-$k_z$ plane using a Cartesian trajectory with spiral profile ordering. The MR image sequence for generating the 3D CMRA data in this example implementation is a 3D balanced steady-state free precession (bSSFP) sequence, which may be ECG-triggered.

The present disclosure is not limited to the particular k-space acquisition procedure of the example of FIG. 1. In particular, the present disclosure is not limited to 3D whole heart CMRA. Imaging other regions of the subject, such as the liver is within the scope of the present disclosure. Further, obtaining 2D image regions rather than 3D image regions is within the scope of the present disclosure. Further, the present disclosure is not limited to Cartesian sampling, other forms of sampling such as radial sampling and radial sampling with golden angle separation are within the scope of the present disclosure. Further, the present disclosure is not limited to bSSFP sequences. Other MR image sequences such as gradient echo sequences are within the scope of the present disclosure.

Steps 102 and 103 comprise using a sparse image coding procedure to reconstruct the MR image data from the k-space data, the sparse image coding procedure comprises using a sparse image coding procedure to reconstruct the MR image data from the k-space data by iteratively solving an optimization problem comprising a data consistency iteration step 102, and a denoising iteration step 103 applied to MR image data generated by the data consistency iteration step The first time step 102 is implemented there is no prior information (from step 103), however, each subsequent application of step 102 incorporates the output of step 103 as input 104 in an iterative reconstruction The denoising iteration step 103 incorporates a sparsifying operation to provide a sparse representation of the MR image data for the imaged region as an input (104) to the data consistency iteration step of the optimization problem.

The present disclosure is not limited to the correcting procedure of FIG. 1. Other ways for correcting for motion are within the scope of the present disclosure. Further, the present disclosure does not require that the motion is corrected for in all embodiments.

Two-dimensional image based navigators (iNAVs) were acquired at each cardiac cycle. These low spatial resolution iNAV images are acquired in every heartbeat before the MRI data acquisition. This technique provides a set of images with high-temporal resolution which are then used to estimate respiratory motion of the heart. This approach has the advantage to spatially isolate the moving heart from the surrounding static tissues and also avoid the use of gating window, therefore increasing the total scan efficiency to or close to 100%. Higher scan efficiency also means predictable and shorter scan times. The k-space data is motion-corrected by applying phase shift correction, with the shift values being estimated in the image domain from the iNAVs directly using rigid motion correction.

Figure 2:
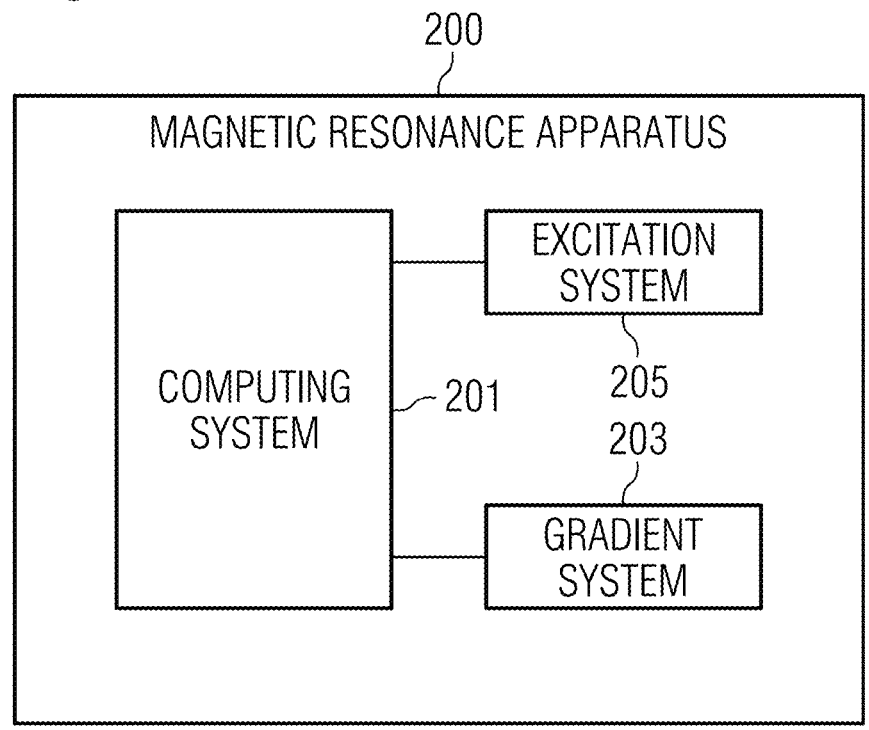
FIG. 2 shows an example MR apparatus according to the second aspect of the present disclosure.

Referring to FIG. 2, there is shown an example MR apparatus 200 according the second aspect of the disclosure. The MR apparatus 200 comprises a computing system 201, a gradient system 203, and an excitation system 205.

The gradient system 203 is configured to apply a magnetic field gradient. The gradient system 203 may be configured to apply magnetic field gradients along three spatial axes.

The excitation system 205 may comprise a transmitter (not shown) and a receiver (not shown). The excitation system 205 can be an RF system with one or more RF coils (not shown). The excitation system 205 is configured to apply an excitation pulse to the subject and to receive signals from the subject.

The MR apparatus 200 includes a magnet (not shown) for establishing a stationary magnetic field. The magnet can include a permanent magnet, a superconducting magnet or other type of magnet.

The computing system 201 is in communication with the excitation system 205, and the gradient system 203 for controlling these components. The computing system 201 is configured to receive the signals from the excitation system 205.

The computing system 201 is further configured to execute program code to control the gradient system 203 and the excitation system 205 to acquire k-space data of an image region of a subject, and a plurality of navigator signals for the image region of the subject.

The computing system 201 is further configured to use a sparse coding procedure to reconstruct the MR image data from the k-space data. The sparse coding procedure comprises solving an optimization problem comprising a data consistency iteration component and a denoising/sparsity component.

The computing system 201 is configured to execute program code for controlling the MR apparatus 200 to perform the method of the first aspect. The computing system 201 could be an integrated component of the MR apparatus 200. The computing system 201 could be a unit of a desktop computer, a workstation, a server, or a laptop computer.

According to aspects of the disclosure, there is also provided a computer-readable medium having instructions recorded thereon which, when executed by a processing unit, cause the processing unit to perform the method of the first or second aspect.

In other words, computing system is in communication with the excitation system, and the gradient system for controlling these components, and is configured to receive the signals from the excitation system. The computing system is further configured to execute program code to control the gradient system and the excitation system to acquire k-space data of an image region of a subject. The computing system is configured to use a sparse image coding procedure to reconstruct the MR image data from the acquired k-space data by iteratively solving an optimization problem comprising a data consistency iteration step and a denoising iteration step applied to MR image data generated by the data consistency iteration step. The denoising iteration step incorporates a sparsifying operation to provide a sparse representation of the MR image data for said imaged region as an input to the data consistency iteration step of the optimization problem. The computing system may be further configured to obtain a plurality of navigator signals for the image region of the subject.

Data Acquisition:

A prototype under-sampled Cartesian variable density 3D spiral-like Cartesian sampling (VD-CASPR) was implemented on a 1.5T scanner (Siemens, Aera). A 2D image-navigator precedes each VD-CASPR acquisition to enable beat-to-beat 2D translational respiratory motion estimation/correction without data rejection. Five healthy volunteers (3 females, 30±4 years) underwent free-breathing CMRA. Data were acquired in middiastole with an ECG-gated 3D bSSFP sequence, 18-channel body and 32-channel spine coils, fat-saturation and T2-preparation pulses (FOV=320× 320×120 mm3, TR/TE=3.35/1.47 ms, FA=90°, bandwidth=890 Hz/pixel, T2-preparation duration=40 ms) with 1.2 mm³ isotropic resolution and under-sampling factors of 5 and 9.

Figure 4:
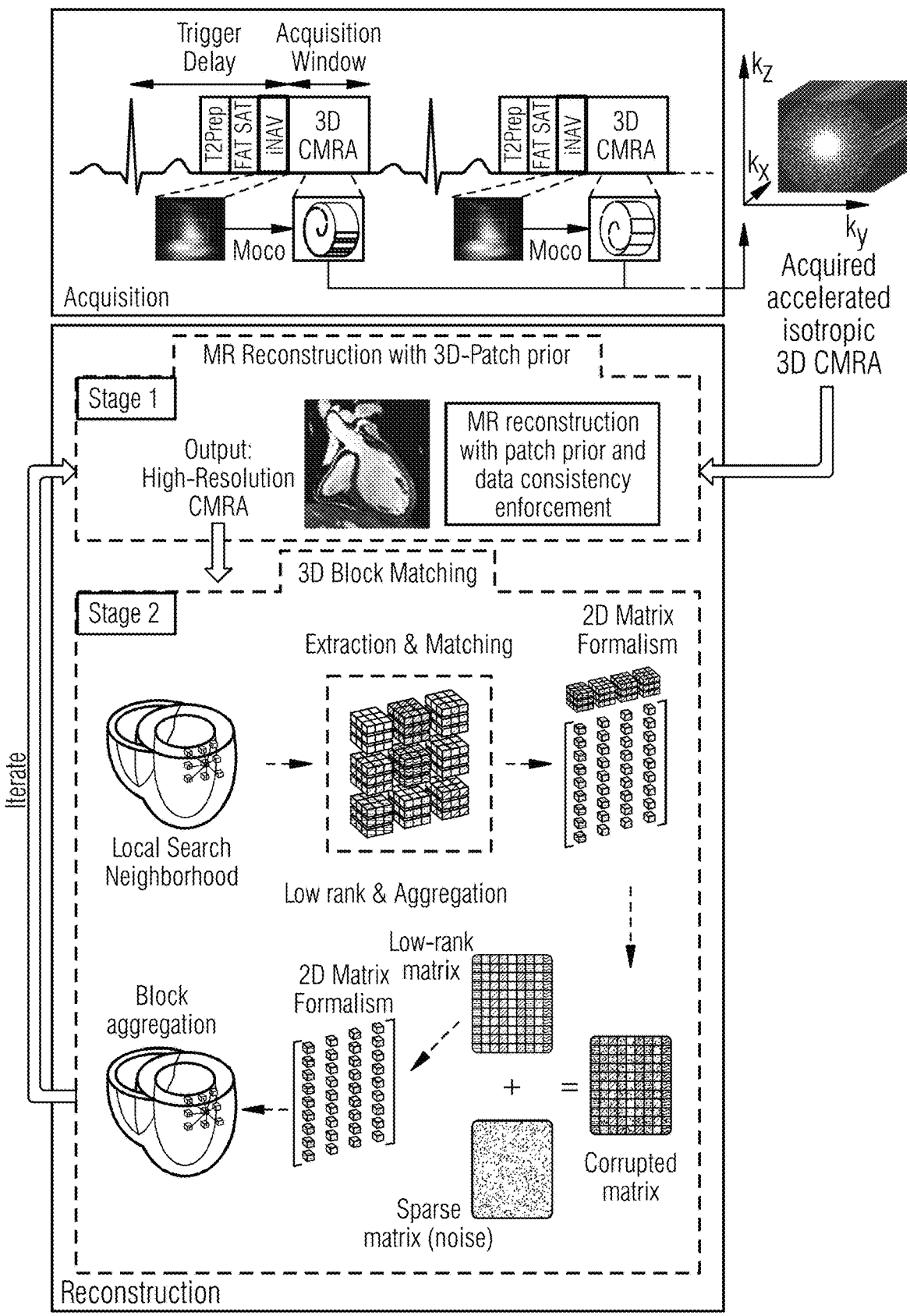
FIG. 4 shows an implementation of an embodiment of the disclosure upon 3-dimensional (3D) MRI data.

Reconstruction:

The disclosure, in a preferred embodiments, was implemented and is herein denoted the '3D-Patch-based low-rank ReconstructiOn with Self-similariTy learning (3D-PROST)' method. This integrates anatomical structure information from 3D patch neighbourhoods through sparse representation, exploiting the redundancy of 3D patches in the acquired data itself. The optimization problem iterates between a data consistency step, which reconstructs a high-resolution isotropic MR volume x, and a low-complexity 3D patch-based denoising step, which provides a reconstructed volume as prior for the next step (FIG. 4).

The two sub-problems are solved iteratively in an effective Augmented Lagrangian (AL):

$$\mathcal{L}(x, \alpha) = \underset{x,\alpha}{\mathrm{argmin}}\left\{\frac{1}{2}\|Ex - k\|_2^2 + \lambda\|\alpha\|_0 + \frac{\mu}{2}\|x - D\alpha - b\|_2^2\right\}$$

Here, λ is a sparsity-control parameter the value of which is adjustable to adjust the strength of sparsity for the sparse representation of the MR image data, μ is a regularization parameter, α is a (sparse) coefficient vector associated with a dictionary matrix (D), and b is the Augmented Lagrangian multiplier. Here, E is the encoding operator (including coils, Fourier operator and sampling), x denotes the undersampled data, D is also the patch-grouping operator (synthesis dictionary). The $\|\ \|_0$ norm counts the number of non-zeros element in α and λ>0 controls the strength of sparsity.

The two problems are solved iteratively:

Iteration Step:

MR Stage 1:
  MR reconstruction (FIG. 4: Stage 1) is performed using a conjugate gradient (CG) descent and uses the 3D denoised volume (x=Dα) obtained from Stage 2 as prior knowledge (x=b=0 initially, then updated by Stage 2). The data consistency iteration step is of the form of an Augmented Lagrangian:

$$\mathcal{L}_1(x) = \underset{x}{\mathrm{argmin}}\left\{\frac{1}{2}\|Ex-k\|_2^2 + \frac{\mu}{2}\|x-D\alpha-b\|_2^2\right\}$$

Iteration Stage 2:

A 3D block-matching 2,5 algorithm is used to exploit redundancies in the volume x. The most similar 3D blocks to a reference block are extracted, vectorised and concatenated into a 2D matrix. Sparsity of this low-rank matrix is enforced using complex Singular Value Decomposition (SVD) and by hard thresholding the singular values below a specific threshold A. The de-noised 3D blocks are then placed back to their original positions by averaging (FIG. 4: Stage 2). The denoising iteration step takes the of the form of an Augmented Lagrangian:

$$\mathcal{L}_2(\alpha) = \underset{\alpha}{\mathrm{argmin}}\left\{\frac{1}{2}\|x-D\alpha-b\|_2^2 + +\lambda\|\alpha\|_0\right\}$$

Implementation and Analysis:

The following parameters were empirically selected to provide the best reconstruction quality: patch_size=5×5×5 voxels, window_search=14×14×14 voxels, AL_iterations (stages 1 and 2 above)=4, CG_iterations=30, $\lambda$=4, $\mu$=1. The proposed approach was compared to conventional zero-filled (ZF), iterative-SENSE, and Wavelet-based Compressed Sensing (CS) reconstructions.

A prototype free-breathing 3D whole-heart, electrocardiogram (ECG)-triggered, balanced steady-state free precession (bSSFP) sequence with variable density Cartesian undersampling was implemented. The $k_y$–$k_z$ phase-encoding plane was sampled following approximate spiral interleaves on the Cartesian grid with variable density along each spiral arm. One spiral arm is acquired per cardiac cycle and is then rotated from one cardiac cycle to the next one. The $k_y$–$k_z$ plane is then segmented in two sets of concentric rings, the first defining the fully-sampled k-space centre and the second representing the accelerated spiral branches.

The phase-encoding lines within each ring were sorted according to a defined increment angle from 0 to 360°. The sampling of the accelerated branches is accelerated exponentially from the k-space centre to its periphery. The size of the fully-sampled k-space centre was optimized on several datasets and was set to 20% the size of $k_y$ and $k_z$ encoding directions. This under-sampled trajectory ensures a pseudo-random pattern through the cardiac cycle, resulting in incoherent aliasing which spreads irregularly in a noise-like fashion.

The acquisition of each spiral arm was preceded by a 2D iNAV to enable beat-to-beat 2D translational (SI: superior-inferior, RL: right-left) respiratory motion estimation/compensation and 100% scan efficiency. iNAVs were obtained by spatially encoding 14 startup echoes of the bSSFP CMRA sequence. 2D translational motion may be estimated using a template-matching algorithm, with the template selected around the heart during acquisition planning. Motion compensation may be performed by modulating the k-space data with a linear phase shift to a reference position at end-expiration. Motion estimation/compensation may be performed before 3D-PROST reconstruction and may be implemented inline in the scanner software. The acquisition framework is depicted in the sequence diagram of FIG. 4a.

In FIG. 4—'Data Acquisition':

Motion correction is performed with an under-sampled 3D variable density spiral-like Cartesian trajectory, (VD-CASPR) preceded by 2D image navigators (iNAV), T2 preparation and fat saturation pulses. iNAVs were used to estimate and correct for the beat-to-beat 2D translational respiratory-induced motion of the heart (Moco).

In FIG. 4—'Reconstruction':

The 3D-PROST reconstruction involves two stages of an Augmented Lagrangian optimization scheme as described above. In stage 1, image reconstruction is performed with patch prior and data consistency enforcement. In stage 2, image denoising is performed using 3D block-matching, which groups similar 3D patches in the image, followed by a low-rank approximation of each group using 2D-SVD shrinkage. The de-noised volume from stage 2 is used in the reconstruction process in stage 1 as prior knowledge to guide the reconstruction problem and further reduce the noise.

The general formulation of sparse representation in terms of a redundant dictionary considers a 3D image I as the approximation I≈D$\alpha$, where D is a fixed dictionary and $\alpha$ a sparse vector satisfying the sparsity-inducing condition:

$$\|\alpha\|_0 \leq T,$$

where the $l_0$-norm counts the number of nonzero elements in $\alpha$ and T is a predefined threshold. Strictly speaking, the image I can be represented with a minimum number of sparse coefficients $\alpha$ in the redundant dictionary D. In the present embodiment, a novel reconstruction algorithm is used which iteratively exploits the structure redundancy in the acquired data I to construct a specific dictionary D for each group of similar 3D patches. The 3D-PROST scheme for isotropic CMRA reconstruction using 3D patch redundancy is formulated as the following unconstrained optimization on the sparse coefficients $\alpha$:

$$\underset{\alpha}{\mathrm{argmin}}\left\{\frac{1}{2}\|AFS_cD\alpha-k\|_2^2 + \lambda\|\alpha\|_0\right\}$$

Where $S_c$ are the known coil sensitivities for channel c, F is the Fourier transform, A is the sampling operator, k is the acquired multi-channel k-space data, and $\lambda$ is the regularization parameter.

The data acquired by each coil (the $c^{th}$ coil) can be expressed in the form:

$$m_c = AFS_cI$$

Here, I=D$\alpha$, is the image series to be reconstructed and $m_c$ is the acquired data for the $c^{th}$ coil element of MRI apparatus, and the coil sensitivities $S_c$ for the coil/channel c may be in the form of a sensitivity map in the space (e.g. Cartesian: x-y) of the image. To implement multi-coil imaging (parallel image reconstruction) the image data from the individual coil elements/channels are concatenated such that:

$$m = \begin{bmatrix} m_1 \\ \vdots \\ m_j \end{bmatrix} \text{ and } E = A \cdot F \cdot \begin{bmatrix} S_1 \\ \vdots \\ S_j \end{bmatrix},$$

where j is the number of coils, then one may employ the multi-coil imaging (parallel image reconstruction) of data acquired by all j coils:

$$m = EI$$

One may transform the above minimisation equation into its equivalent constrained minimization problem:

$$\underset{I,\alpha}{\mathrm{argmin}}\left\{\frac{1}{2}\|EI-k\|_2^2+\lambda\|\alpha\|_0\right\} \text{ subject to } I=D\alpha$$

Where I denotes the image to recover. This optimization problem is difficult to solve directly due to the constrained form of the functional. The present embodiment solves this minimization problem using its Augmented Lagrangian formulation, which implies minimizing the augmented Lagrangian L, defined below, with regards to I and α:

$$\mathcal{L}_{3DPROST}(I,\alpha)=\underset{x\alpha}{\mathrm{argmin}}\left\{\frac{1}{2}\|EI-k\|_2^2+\lambda\|\alpha\|_0+\frac{\mu}{2}\|I-D\alpha-b\|_2^2\right\}$$

Here, b represents the Lagrange multiplier associated with the constraint "I=Dα", and μ≥0 is the penalty parameter. This equation is solved using a variable splitting approach by alternating the minimization with respect to the image I (Iteration Stage 1) and the sparse coefficients α (Iteration Stage 2), followed by an update of the augmented multiplier b, and repeating these three steps until a convergence criterion is satisfied. The rationale behind this splitting approach is that each sub-problem of this alternating minimization is much simpler to solve than the original unconstrained problem.

ITERATION STAGE 1: MR Reconstruction Update

The first sub-problem with regards to the variable I is a conventional MR reconstruction that incorporate the denoised volume Dα (obtained at the end of stage 2), as prior information:

$$\mathcal{L}_1(I)=\underset{x}{\mathrm{argmin}}\left\{\frac{1}{2}\|EI-k\|_2^2+\frac{\mu}{2}\|I-D\alpha-b\|_2^2\right\}$$

Differentiating with respect to I, we find that the residual gradient step is:

$$m=E^H EI - E^H K + \mu(I-\omega-b)$$

Where the operator $E^H$ denotes the Hermitian transpose of E and ω=Dα represents the truncated SVD reconstruction obtained at iteration stage 2. For the initialization, ω and b were set to 0, which reduce the reconstruction problem to a standard iterative SENSE with Tikhonov regularization. The gradient descent optimization method may be used to iteratively update the reconstructed volume I:

$$I^{(t+1)} \leftarrow I^{(t)} - \beta m^{(t)}$$

Here, the relaxation parameter β can be updated iteratively or be set to a specific value (e.g. β=0.1) to ensure convergence.

ITERATION STAGE 2: 3D Patch-Based Denoising Update

The second sub-problem minimizes with respect to the sparse coefficients α and is given by:

$$\mathcal{L}_2(\alpha)=\underset{\alpha}{\mathrm{argmin}}\left\{\frac{1}{2}\|I-D\alpha-b\|_2^2++\lambda\|\alpha\|_0\right\}$$

Considering that sparse image coding is a local model representation and that neighbouring patches in CMRA images are highly redundant, this optimization can be performed on an image patch basis. A 3D patch $I_k$ in the previously reconstructed (at Iteration Stage 1) volume I of size N voxels is defined as a small 3D block of size $n^3$ voxels around the voxel at index k.

Define the operator $R_k$ that extracts the patch $I_k$ from the image I: $I_k=(I)$. Inversely, one can recover the image I from its set of patches in a straightforward manner:

$$I=(\Sigma R(I_k))./(\Sigma R_k^H R_k)=(\Sigma R_k^H(D_k\alpha_k))./(\Sigma R_k^H R_k), \text{ for } k=1 \text{ to } N.$$

Where the operator $R_k^H R_k$ is a matrix of same size as $I_k$ with all elements being 1 (i.e. averaging matrix), (α,) represents the concatenation of all ($\alpha_{k,k}$) and the operator "./" denotes the element-wise division. The above equation can thus be rewritten as the following patch-based minimization given by:

$$\underset{\alpha}{\mathrm{argmin}}\left\{\frac{1}{2}\|I_k-D_k\alpha_k-b_k\|_2^2++\lambda\|\alpha_k\|_0\right\} \text{ for } k=1,\ldots,N$$

Efficient optimization is achieved through the choice of the dictionary $D_k$ which induces the highest sparsity in its associated group of similar patches, and how accurately the sparse coefficients $\alpha_k$ can be recovered from this dictionary. In 3D the present patch-based representation, the self-similarity is considered as a 4D set of similar 3D patches $[I_1, \ldots, I_k]$ selected in a large 3D window d, and its associated sparse coefficients $[\alpha_1, \ldots, \alpha_L]$ obtained from a dictionary $D_k$. In order to account for 3D patches, the present embodiment reduces the complexity of the problem by concatenating each similar vectorized 3D patch into a 2D matrix. This 2D matrix, containing a high degree of similarity, exhibits a low-rank structure which can be sparsely approximated using singular value decomposition (SVD). Using the unitary property of the SVD, the minimization problem of the above equation is equivalent to minimizing with regards to the sparse coefficients the following equation, $$\mathcal{L}_2(\alpha)=\underset{\alpha_k}{\mathrm{argmin}}\left\{\frac{1}{2}\|\tilde{\alpha}_k-\alpha_k\|_2^2++\lambda\|\alpha_k\|_0\right\}$$

Where $\tilde{\alpha}_k$ are the sparse coefficients associated with $I_k-b_k=\tilde{I}_k$ and λ>0 controls the strength of sparsity. The lower the parameter λ, the more accurate the reconstructed solution, at the price of reducing the sparseness. The solution of the above equation has a closed form, and the optimum is obtained using hard-thresholding:

$$\alpha_k^* = H_{\sqrt{2\lambda}}(\tilde{\alpha}_k)$$

Here, $H_0(.)$ is the element-wise hard-thresholding operator, defined for a scalar v as: $H_0(v)=0.1_{|v|>0}$. In other words, any singular values $\tilde{\alpha}_k$ below $\sqrt{2\lambda}$ is set to 0. Note that only the singular values are modified, but the singular vectors are unperturbed. The value $\alpha_k^*$ is indirectly an estimate of the noise $\tilde{I}_k=I_k-b_k$, and thus the hard-thresholding step effectively shrinks the noise.

This step is repeated for each voxel in the volume I and the final de-noised 3D volume ω=Dα is obtained by aggregating the multiple estimates $D_k\alpha_k^*$ at each voxel location k=1, . . . . The Lagrange multiplier is then updated at iteration t+1 as:

$$(t+1) \leftarrow (t) + r(\omega^{(t+1)}-I^{(t+1)})$$

Where the penalty parameter r is set to an appropriate value (e.g. set to 0.1). Optimizations for Stage 1 and Stage 2 are processed iteratively to improve the accuracy of the reconstructed volume. A flowchart illustrating all steps is shown in FIG. 4b.

Image Reconstruction Implementation

Important parameters of interest are the size of patch n, size of neighbourhood window d, number of selected patches L, regularization parameters λ and μ, as well as the number of outer iterations. The size of patch n controls the degree of structural information within each patch. On one hand, a large value of n would capture the most geometric information and leads to a higher level of denoising, while a small value would act as a local filter and would potentially reduce the denoising performance of the algorithm.

An example is to set the size of patches to be 5×5×5 voxels and the selection window d to 14, which gives a good trade-off between reconstruction quality and computation time. The number of selected similar patches L may be set to 40 to avoid high computation cost and excessive memory requirements associated with large values of L. The performance of 3D-PROST may be used, for example, with the values λ=0.1 and μ=0.3.

3D-PROST reconstruction was compared to iterative SENSE (itSENSE) and a CS reconstruction with wavelet regularization, as implemented in the BART toolbox. The regularization parameter was carefully tuned and set to λCS=0.01 in all studies and the algorithm was stopped after 30 iterations (respectively five for itSENSE), since preliminary testing revealed that these numbers of iterations led to the best reconstructions.

Phantom Study

Acquisition:

A phantom acquisition was performed to evaluate the impact of highly under-sampled acquisitions on the reconstructed resolution. The phantom was composed of parallel bar patterns with in-plane resolution of 1 mm. The relevant imaging parameters were as follows: 3D bSSFP sequence, field-of-view (FOV)=306×306×80 mm3, TE=1.63 ms, TR=3.7 ms, flip angle (FA)=90°, 0.9 mm$^3$ isotropic resolution, sampling bandwidth=875 Hz/pixel, T2-preparation duration=40 ms.

Acquisitions were performed with under-sampling factors of 5 and 9. Additionally, a fully-sampled acquisition was performed for comparison purposes.

Acquired motion-corrected data was reconstructed with itSENSE, CS and the 3D-PROST of the present embodiment. Under-sampled reconstructions were compared against the fully-sampled reference images. Reconstructed images were reformatted along the right (RCA) and left anterior descendent (LAD) coronary arteries and visible vessel length and vessel sharpness (first 4 cm and full length) were measured. A vessel sharpness of 100% marked an abrupt change in signal intensity whereas a sharpness of 0% indicated the absence of an edge.

Data Analysis:

The modulation transfer function (MTF) was used to quantify the spatial resolution for the under-sampled and fully sampled reconstructions. The MTF was directly obtained using a slanted edge method. A profile (edge spread function) was taken along a sharp edge of the phantom, then differentiated to obtain the associated line spread function, and finally fast Fourier transformed to get the final MTF, which was then normalized. The reconstructed resolution was given by the value of the MTF at 10%. The MTF was obtained from 20 intensity profiles taken on the reference fully-sampled image, the zero-filled (ZF) reconstruction and the 3D-PROST reconstructions. The average MTFs were compared for both accelerations. A paired two-tailed Student t-test was used for statistical analysis, with P<0.05 considered statistically significant.

Results:

Phantom Study:

The total scan times (min:sec) were 11:30 (fully-sampled), 2:13 (5-fold acceleration) and 1:15 (9-fold acceleration) with isotropic resolution of 0.9 mm$^3$.

Figure 5:
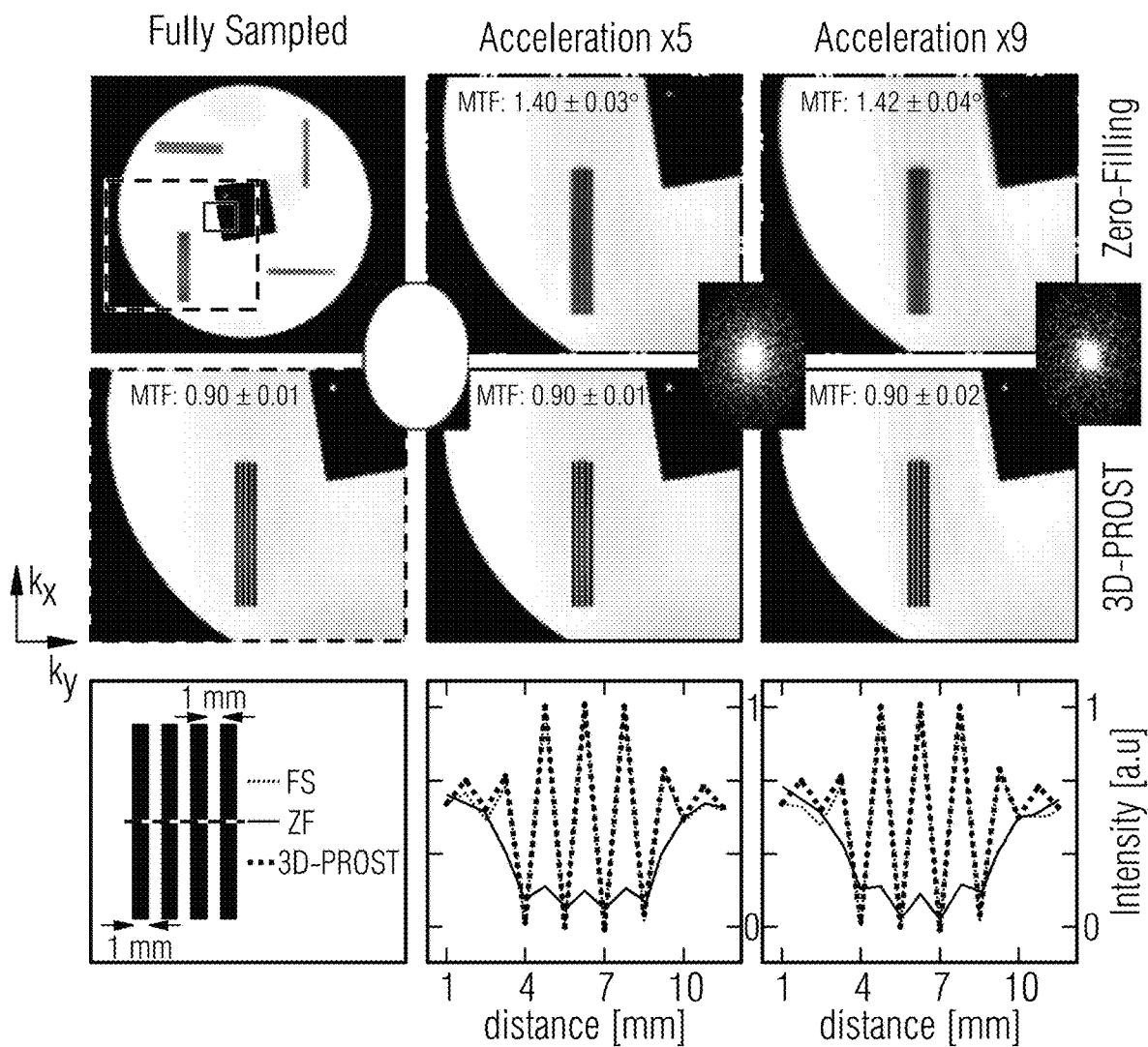
FIG. 5 shows examples for the application of the embodiment ("3D-PROST") of FIG. 4 on a high-resolution phantom. Fully sampled acquisition (FS-left column) is compared to 5-fold and 9-fold accelerated acquisitions (middle and right columns respectively), for both zero-filled (ZF-top row) and 3D-PROST (middle row) reconstructions. The variable density under-sampled Cartesian images with ZF reconstruction show significant blurring and contrast loss, while the 3D-PROST images exhibit sharp edges with faithful preservation of small details (as shown on the cross-section profiles). Reconstructed resolution for ZF and the proposed 3D-PROST technique are shown on the top-left corner (MTF-profiles taken in the region-of-interest box). Differences with statistical significance are identified by *P<0.05 (versus FS).

The reconstructed images using ZF and 3D-PROST are shown in FIG. 5 in comparison with the reference fully-sampled image. The measured MTFs are shown on the top of each image. Significant aliasing artifacts can be observed on the ZF images, and were particularly pronounced for high undersampling where the depiction of the bar pattern becomes indistinguishable. Conversely, high image quality can be appreciated using the 3D-PROST reconstruction of the present embodiment, with clear and sharp depiction of the phantom structures with high spatial resolution, even for high acceleration (×9), providing excellent visual agreement with the reference fully-sampled image. This observation is confirmed and illustrated in FIG. 5 (bottom) where the intensity profiles taken perpendicularly across the pattern are plotted for each reconstruction. The fine and sharp structures of the bars are well preserved with 3D-PROST reconstruction while ZF reconstruction exhibits blurring and loss of contrast. The spatial resolution, as quantified by the MTF, was preserved with the proposed approach, showing no statistical differences with the reference fully-sampled image (5-fold: 0.90±0.01, P=0.31 and 9-fold: 0.90±0.02, P=0.17).

2D-PROST:

The disclosure may be implemented to reconstruct 2-dimensional (2D) MRI data, herein referred to as the 2D-PROST reconstruction embodiment. This may be performed with the same parameters as 3D-PROST except for the size of the patches (for example: 2D: 5×5 voxels vs. 3D: 5×5×5 voxels) and the selection window d (for example: 2D: 5×5 voxels vs. 3D: 5×5×5 voxels).

DISCUSSION

The proposed 3D-PROST reconstruction embodiment integrates self-similarity information, by grouping 3D patches with similar structures. Low-rank properties and sparsity of the group are enforced to reduce the noise of the reconstructed volume while the MR reconstruction step was used to recover an isotropic 3D volume and enforce data fidelity. An Augmented Lagrangian formulation efficiently decomposes the main cost function into two sub-problems that have straightforward solutions. The improved performance can be explained by the fact that CMRA images contain a rich amount of correlated 3D structures and therefore high sparsity degree can be achieved by merging this information. The increased sparsity promotes superior denoising and structures recovery in comparison to other established approaches. Similar image quality was achieved for an isotropic 1.2 mm$^3$ resolution.

Under-sampled reconstruction according to the disclosure, may be used to obtain isotropic sub-millimetre 3D coronary images under free-breathing in ~5 min predictable scan time, which is crucial for its integration in routine clinical examinations.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements.

The described and illustrated embodiments are to be considered as illustrative and not restrictive in character, it being understood that only the preferred embodiments have been shown and described and that all changes and modifications that come within the scope of the embodiments as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the disclosure. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

Although a few preferred embodiments have been shown and described, it will be appreciated by those skilled in the art that various changes and modifications might be made without departing from the scope of the disclosure.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention claimed is:

1. A method of reconstructing a magnetic resonance (MR) image from k-space data, the method comprising:
providing a computer with k-space data of an image of a subject; and
in said computer, performing a reconstructing algorithm, using a sparse image coding procedure in order to reconstruct, the MR image from the k-space data with iterative optimization comprising:
a data consistency iteration step comprising a determination of a difference between the reconstructed MR image transformed into k-space and the provided k-space data, wherein the determination of the difference comprises determining an $l_2$-norm of the result of the difference between the provided k-space data and the reconstructed MR image transformed into k-space; and
a denoising iteration step applied to an MR image generated by the data consistency iteration step, wherein the denoising iteration step incorporates a sparsifying operation to provide a sparse representation of the MR image for the imaged region as an input to the data consistency iteration,
wherein the denoising iteration step is of the form $$\hat{x} = \operatorname*{argmin}_{x} h(x), h(x),$$

h(x) is a function defined as {sparse consistency component in image space+λ(sparse coefficients associated with a synthesis dictionary for the sparse representation of the MR image data)}, and λ is a sparsity-control parameter a value of which is adjustable to adjust a strength of sparsity for the sparse representation of the MR image.

2. A method as claimed in claim 1, wherein the data consistency iteration step comprises minimising an Augmented Lagrangian with respect to the reconstructed MR image.

3. A method as claimed in claim 1, wherein the denoising iteration step comprises minimising an Augmented Lagrangian with respect to sparse coefficients associated with a synthesis dictionary for the sparse representation of the MR image.

4. A method as claimed in claim 1, wherein the denoising iteration step comprises a determination of the difference between the reconstructed MR image and the sparse representation of the MR image.

5. A method as claimed in claim 4, wherein the determination of the difference comprises determining a $l_2$-norm of a result of a subtraction of the sparse representation of the MR image from the reconstructed MR image.

6. A method as claimed in claim 1, wherein the data consistency iteration step of an optimization problem is of the form $$\hat{x} = \operatorname*{argmin}_{x} f(x),$$

wherein $f(x)$ is a function defined as {data consistency component in k-space+μ(sparse consistency component in image space)}, wherein μ is a regularization parameter.

7. A method as claimed in claim 1, wherein the sparsifying operation of the denoising iteration step is applied to sparse coefficients associated with a synthesis dictionary for the sparse representation of the MR image, whereby sparse coefficients having a value below a threshold value are set to zero.

8. A method as claimed in claim 7, wherein the threshold value is equal to the value of the sparsity-control parameter.

9. A non-transitory computer readable medium comprising instructions recorded thereon which, when executed by a computer, cause the computer to perform the method as claimed in claim 1.

10. A magnetic resonance (MR) apparatus, comprising:
a gradient system configured to apply a magnetic field gradient;
an excitation system configured to apply an excitation pulse to a subject and to receive signals from the subject; and
a computing system configured:
to receive the signals from the excitation system,
to execute program code to control the gradient system and the excitation system to acquire k-space data of an image of a subject, and a plurality of navigator signals for the image of the subject, to reconstruct, using a sparse image coding procedure, an MR image from the acquired k-space data by performing an iterative optimization method comprising:

a data consistency iteration step comprising a determination of a difference between the reconstructed MR image transformed into k-space and the provided k-space data, wherein the determination of the difference comprises determining an $l_2$-norm of the result of the difference between the provided k-space data and the reconstructed MR image transformed into k-space; and a denoising iteration step applied to MR image generated by the data consistency iteration step, wherein the denoising iteration step incorporates a sparsifying operation to provide a sparse representation of the MR image for the image of the subject as an input to the data consistency iteration step.

* * * * *